United States Patent
Liu et al.

(10) Patent No.: US 11,839,219 B2
(45) Date of Patent: Dec. 12, 2023

(54) BVP10 PROTEIN FOR CONTROLLING TETRANYCHID MITES AND USE THEREOF

(71) Applicant: Hubei Biopesticide Engineering Research Center, Hubei (CN)

(72) Inventors: Xiaoyan Liu, Hubei (CN); Ling Chen, Hubei (CN); Yong Min, Hubei (CN); Ronghua Zhou, Hubei (CN); Ben Rao, Hubei (CN); Yan Gong, Hubei (CN); Yimin Qiu, Hubei (CN); Lei Zhu, Hubei (CN); Xianqing Liao, Hubei (CN); Wei Chen, Hubei (CN); Zhigang Cao, Hubei (CN); Liqiao Shi, Hubei (CN); Jingzhong Yang, Hubei (CN)

(73) Assignee: Hubei Biopesticide Engineering Research Center, Wuhan (CN)

( * ) Notice: Subject to any disclaimer, the term of this patent is extended or adjusted under 35 U.S.C. 154(b) by 0 days.

(21) Appl. No.: 17/680,271

(22) Filed: Feb. 24, 2022

(65) Prior Publication Data
US 2023/0019438 A1 Jan. 19, 2023

(30) Foreign Application Priority Data
Jul. 5, 2021 (CN) .......................... 202110755729.X

(51) Int. Cl.
*A01N 63/50* (2020.01)
*C07K 14/00* (2006.01)

(52) U.S. Cl.
CPC .............. *A01N 63/50* (2020.01); *C07K 14/00* (2013.01)

(58) Field of Classification Search
CPC ................................ A01N 63/50; C07K 14/00
See application file for complete search history.

(56) References Cited

U.S. PATENT DOCUMENTS

2015/0282483 A1* 10/2015 Sawada .................. A01N 43/56
424/93.46

OTHER PUBLICATIONS

ID No. 2, Examiner generated PDF, Jan. 5, 2023. Genbank ACCESSION_CAE11241, Pub: Jul. 26, 2016, Examiner generated PDF, https://www.ncbi.nlm.nih.gov/protein/CAE11241.1/ (Year: 2016).*
*Panonychus* Spp. Information 2019, Examiner generated [Jan. 12, 2023 4:30:34 PM] pdf, https://web.archive.org/ . . . p://idtools.org/id/mites/invasive_mite/Invasive_Mite_Identification/key/Tetranychinae/Media/Html/Panonychus.htm, Archived: Jul. 26, 2019 (Year: 2019).*
Pruitt, The Karr Center, Internet archive screenshot, Pub: Aug. 28, 2020, examiner generated PDF, https://web.archive.org/web/20200828044733/https://kerrcenter.com/biopesticides-for-strawberry-plasticulture-in-high-tunnels/ (Year: 2020).*

(Continued)

*Primary Examiner* — Kevin S Orwig
*Assistant Examiner* — John Michael Cronin
(74) *Attorney, Agent, or Firm* — MEI & MARK LLP; Manni Li

(57) ABSTRACT

A BVP10 protein shown in SEQ ID NO:2 for controlling tetranychid mites and use of the protein is provided. The BVP10 protein has a median lethal concentration of 19.07 μg/mL against *Tetranychus urticae*, a median lethal concentration of 58.05 μg/mL against *Panonychus citri*, a median lethal concentration of 36.08 μg/mL against *Tetranychus cinnabarinus*, and a control effect of 79.53%-95.45% against strawberry red spider mites. The protein is provided for preparing a novel mite pesticide.

6 Claims, 1 Drawing Sheet
Specification includes a Sequence Listing.

(56) References Cited

OTHER PUBLICATIONS

Bacillus velezensis FZB42 Taxonomy, Schoch CL, et al. NCBI Taxonomy: a comprehensive update on curation, resources and tools. Database (Oxford). 2020: baaa062. PubMed: 32761142 PMC: PMC7408187 (Year: 2020).*

Spider Mite (*Tetranychus urticae*)—Bioline AgroSciencesBioline, Internet archive screenshot, Pub: Nov. 25, 2020, Examiner generated PDF, https://web.archive.org/web/20201125081745/https://www.biolineagrosciences.com/?pests=spider-mite-two-spotted-or-red (Year: 2020).*

*Bacillus velezensis* strian WLYS23 chromosome, complete genome, GenBank: CP055160.1, published on Jun. 23, 2020.

\* cited by examiner

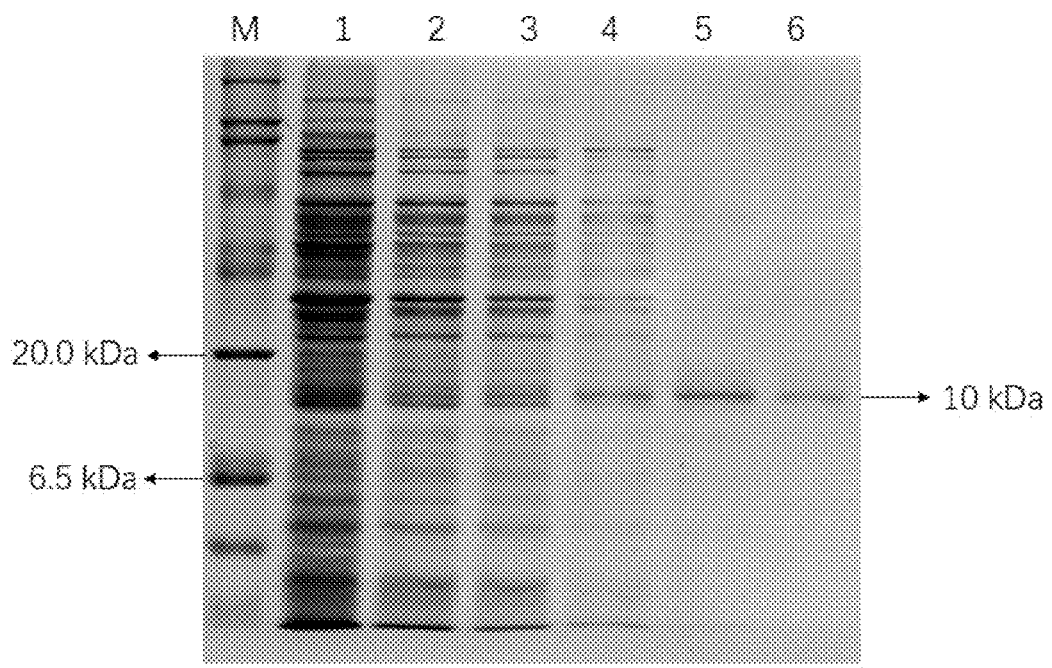

BVP10 PROTEIN FOR CONTROLLING TETRANYCHID MITES AND USE THEREOF

CROSS-REFERENCE TO RELATED APPLICATIONS

The subject application claims priority on Chinese patent application no. 202110755729.X filed on Jul. 5, 2021 in China. The contents and subject matters of the Chinese priority application is incorporated herein by reference.

BACKGROUND OF THE INVENTION

Technical Field

The invention belongs to the technical field of agricultural microbiology, and in particular, relates to a BVP10 protein for controlling tetranychid mites and use thereof.

Description of Related Art

Tetranychid mites, also known as red spider mites or spider mites, are plant-feeding mites of the family Tetranychidae of the subclass Acarina. They eat leaves and fruits of indoor plants and important agricultural plants (including fruit trees). The tetranychid mites go through a life divided into 5 stages, including eggs, larvae, early nymphs, late nymphs, and adults. It takes about three weeks for them to grow from the eggs to the adults. They have a short life cycle and reproduce rapidly, with the course of one generation completed within several days to ten days and the courses of several generations to ten generations completed within one year. This often causes extremely serious damage to crops. The adult mites are red, green, or brown with a length of approx. 0.5 mm, and spin loose webs on plants. When the plants are seriously damaged, the leaves become severely thinned and whitened and even fall off completely. The tetranychid mites can be spread by means of wind, running water, insects, birds, and agricultural implements, or with the transportation of seedlings. Many species of the tetranychid mites have the habit of spinning. In the case of nutrition deterioration, they are able to hang down by spinning to be carried along with the wind.

The mites of the subfamily Tetranychidae infest all the higher plants. The more common genuses include *Tetranychus, Panonychus, Eotetranychus, Oligonychus*, and *Schizotetranychus*. Among them, *Panonychus citri* are widely distributed in citrus production areas across the world, and are major pest mites affecting citrus production. They infest citrus seedlings and trees, and the affected leaves show off-white spots. *Tetranychus urticae* bring harms to vegetables, soybeans, peanuts, corns, sorghums, apples, pears, peaches, apricots, plums, cherries, grapes, cottons, beans, and a variety of other crops and nearly a hundred species of weeds. *Oligonychus perditus* infest cypress trees and are distributed in China and Japan. In drought years, the cypress trees are damaged severely, with crowns yellowing and needle leaves falling off. *Schizotetranychus yoshimekii*, which are distributed in Southwestern China and Thailand, severely infest rice by feeding on the leaves to turn all of the green leaves into greyish-green to off-white. The affected rice plants have short ears and small grains, with the yield reduced by approximately 10%, or up to more than 30% in severe cases.

Methods for controlling the tetranychid mites mainly include agricultural control, biological control, and chemical control. The agricultural control includes clearing orchards in winter, removing and intensively burning diseased leaves to reduce the number of pest mites living through the winter, and reinforcing the management of fertilizer and water to improve the microclimate of orchards, etc. The biological control includes controlling the mites by using green and safe means such as their natural enemies and biologic mite pesticides. The chemical control is mainly to control the mites by using chemicals such as chemical mite pesticides. In recent years, due to the absence of substitute varieties to mite pesticides, the mite pesticides have been used heavily and repeatedly, which has accelerated the generation of resistance in pest mites, resulting in increasingly serious mite damage. This causes great economic losses to growers.

At present, most of the mite pesticides developed in the world are chemical substances or macromolecular antibiotics, which are insoluble in water, and micromolecular proteinaceous substances have been less reported. Therefore, in light of the above background, it is necessary to develop a proteinaceous agent for controlling the tetranychid mites for use in the field of biological control of the tetranychid mites, which is of important significance in production and practice.

BRIEF SUMMARY OF THE INVENTION

An objective of the invention is to provide a protein shown in SEQ ID NO:2 for controlling tetranychid mites.

Another objective of the invention is to provide use of the protein for controlling tetranychid mites in the preparation of a tetranychid mite pesticide.

To achieve the above objects, a technical solution used in the invention is as follows.

A protein for controlling tetranychid mites is shown in SEQ ID NO:2; and a gene encoding the protein shown in SEQ ID NO:2 also falls within the protection scope of the invention. Preferably, the gene is shown in SEQ ID NO:1.

The above protein prepared by conventional methods, such as prokaryotic expression, eukaryotic expression, or direct synthesis, in the art also falls within the protection scope of the invention.

The use of the protein for controlling the tetranychid mites in the preparation of a tetranychid mite pesticide includes the preparation of the tetranychid mite pesticide by taking the protein shown in SEQ ID NO:2 as one of the effective ingredients or as the only effective ingredient.

During the above use, preferably, the tetranychid mites are *Tetranychus urticae, Panonychus citri, Tetranychus cinnabarinus*, or strawberry red spider mites.

Compared with the prior art, the invention has the following characteristics.

The invention reports a novel protein for controlling tetranychid mites and a miticidal activity thereof for the first time, which provides a new option for the preparation of a novel mite pesticide. The mite pesticide prepared from the BVP10 protein according to the invention has the advantages of high efficiency, low toxicity, and environmental friendliness.

BRIEF DESCRIPTION OF THE SEVERAL VIEWS OF THE DRAWINGS

FIG. 1 is a sodium dodecyl sulfate-polyacrylamide gel electrophoresis (SDS-PAGE) analysis chart of a purified BVP10 protein in the present invention.

DETAILED DESCRIPTION OF THE INVENTION

Experimental methods in the embodiments below are all conventional microbiological operation methods that have been ever reported, unless otherwise specified. Reagents or materials as mentioned are all conventional solutions in the art, unless otherwise specified.

The BVP protein of the invention may be prepared by conventional methods, such as prokaryotic expression and commercial synthesis, in the art. The invention illustrates the mite suppression effect of a prokaryotically-expressed BVP protein, by way of example. The same protein derived by other means may also achieve the same effect.

Example 1: Preparation of Miticidal BVP10 Protein (1) Based on the sequence (encoding the protein shown in SEQ ID NO:2) shown in SEQ ID NO:1, BVP10 protein gene fragments (Sangon Biotech (Shanghai) Co., Ltd.) are artificially synthesized, and then bonded to expression vector plasmids pet28a of *Escherichia coli* to construct recombinant expression plasmids pet28a-BVP10.

(2) Expression and Purification of Miticidal BVP Protein in *Escherichia coli* B21

The above recombinant expression plasmids pet28a-BVP10 carrying a coding sequence are transformed into *Escherichia coli* BL21 to prepare recombinant bacteria BL21/pet28a-BVP10. The recombinant bacteria are inoculated into 5 mL of Luria-Bertani (LB) liquid medium, and cultured in a shaker at 37° C. until OD600 is 0.6. 1.0 mmol/L isopropyl-B-D-thiogalactoside (IPTG, Sigma) is added for induced culturing for 3 h at 30° C. 50 mL of a 3-hour induced culture of the above recombinant bacterial BL21/pet28a-BVP10 is centrifuged at 12,000 rpm for 30 s to collect bacterial cells. The bacterial cells are disrupted by ultrasonic waves (technical parameters: 300 W; 30 s; and an interval of 30 s), and then centrifuged at 12,000 for 15 min to obtain supernatant, which is filtered with a filter membrane having a pore size of 0.4 µm to remove impurities. Various proteins are purified by the affinity chromatography for GST fusion proteins. A final purified product is detected by SDS-PAGE, with the results shown in FIG. 1. The purified proteins are compared with a protein molecular weight marker to derive an estimated molecular weight of 10 kDa, which is basically in line with the molecular weight of 10.07 kDa as predicted for the BVP10 protein. This demonstrates the successful expression of the BVP10 protein according to the invention in *Escherichia coli* BL21.

Example 2: Use of BVP10 Protein in the Preparation of Tetranychid Mite Pesticide (1) BVP10 Protein Killing *Tetranychus urticae*:

Referring to the standard method for determining pest mites, namely, the slide dipping method, recommended by Food and Agriculture Organization of the United Nations (FAO), a double-faced adhesive tape is cut into pieces 2-3 cm long and stuck to one end of a microscope slide, and paper on the adhesive tape is removed with tweezers. Female adult mites with similar sizes, bright body color and high vitality are picked with a 0# Chinese writing brush, and are stuck to the double-faced adhesive tape (note: the feet, whiskers, and mouthparts of the mites should not be stuck) on their backs, with 4 lines stuck to each piece and 10 mites in each line. The mites are placed and left in a biochemical incubator for 4 hrs at temperature of 25° C. and a relative humidity of approximately 85%, and then are observed with binoculars. Dead or inactive individuals are eliminated. The agent is diluted 5-7 times with water based on a preliminary test. One end of the slide with the mites is dipped into the agent solution, shaken lightly for 5 s, and then taken out. The mites, as well as the excessive agent solution therearound, are rapidly dried with absorbent paper. The slide is placed and left in the above biochemical incubator. After 24 hrs, the results are checked with the binoculars. The bodies of the mites are lightly touched with the Chinese writing brush, and those without any motion of their feet are considered to be dead. The test is repeated three times at each concentration, and the mites dipped in fresh water are taken as a control. Following the experimental steps above, the bioassay result of a BVP10 protein suspension against *Tetranychus urticae* are shown in Table 1 below, which is 19.07 µg/mL. An $LC_{50}$ value is calculated by using SPASS 19.0 data processing software.

TABLE 1

Miticidal activity of BVP10 protein against *Tetranychus urticae*

| Dose (µg/mL) | Mortality (%) | Logarithmic Dose | Probability Unit (P + 5) | Regression Equation | Medial Lethal Concentration ($LC_{50}$, µg/mL) |
|---|---|---|---|---|---|
| 389.5 | 68.4 | 2.591 | 5.483 | Y = 4.5286 + | 19.07 |
| 77.9 | 55.9 | 1.892 | 5.148 | 0.3682X | |
| 38.95 | 60.6 | 1.591 | 5.268 | (r = 0.8832) | |
| 19.475 | 47.2 | 1.289 | 4.927 | | |

(2) BVP10 Protein Killing *Panonychus citri*:

Referring to the standard method for determining pest mites, namely, the slide dipping method, recommended by the Food and Agriculture Organization of the United Nations (FAO), a double-faced adhesive tape is cut into pieces 2-3 cm long and stuck to one end of a microscope slide, and paper on the adhesive tape is removed with tweezers. Female adult mites with similar sizes, bright body color and high vitality are picked with a 0# Chinese writing brush, and are stuck to the double-faced adhesive tape (note: the feet, whiskers, and mouthparts of the mites should not be stuck) on their backs, with 4 lines stuck to each piece and 10 mites in each line. The mites are placed and left in a biochemical incubator with the temperature of 25° C. and a relative humidity of approximately 85% for 4 hrs, and then are observed with binoculars. Dead or inactive individuals are eliminated. The agent is diluted 5-7 times with water based on a preliminary test. One end of the slide with the mites is dipped into the agent solution, shaken lightly for 5 s and then taken out. The mites, as well as the excessive agent solution therearound, are rapidly dried with absorbent paper. The slide is placed and left in the above biochemical incubator. After 24 hrs, the results are checked with the binoculars. The bodies of the mites are lightly touched with the Chinese writing brush, and those without any motion of their feet are considered to be dead. The test is repeated three times at each concentration, and the mites dipped in fresh water are taken as a control. Following the experimental steps above, the bioassay result of a BVP10 protein suspension against *Panonychus citri* are shown in Table 2 below, which is 58.05 µg/mL. An $LC_{50}$ value is calculated by using the SPASS 19.0 data processing software.

TABLE 2

Miticidal activity of BVP10 protein against *Panonychus citri*

| Dose (µg/mL) | Mortality (%) | Logarithmic Dose | Probability Unit (P + 5) | Regression Equation | Medial Lethal Concentration (LC$_{50}$, µg/mL) |
|---|---|---|---|---|---|
| 389.5 | 78.6 | 2.591 | 5.793 | Y = 3.0472 + 1.1072X (r = 0.9548) | 58.05 |
| 77.9 | 63.6 | 1.892 | 5.349 | | |
| 38.95 | 47.1 | 1.591 | 4.922 | | |
| 19.475 | 23.5 | 1.289 | 4.276 | | |

(3) BVP10 Protein Killing *Tetranychus cinnabarinus*

Following the experimental steps above, the bioassay result of a BVP10 protein suspension against *Tetranychus cinnabarinus* are shown in Table 3 below, which is 36.08 µg/mL. An LC$_{50}$ value is calculated by using the SPASS 19.0 data processing software.

TABLE 3

Miticidal activity of BVP10 protein against *Tetranychus cinnabarinus*

| Dose (µg/mL) | Mortality (%) | Logarithmic Dose | Probability Unit (P + 5) | Regression Equation | Medial Lethal Concentration (LC$_{50}$, µg/mL) |
|---|---|---|---|---|---|
| 389.5 | 94.7 | 2.591 | 6.616 | Y = 2.3766 + 1.6846X (r = 0.9797) | 36.08 |
| 77.9 | 80.0 | 1.892 | 5.840 | | |
| 38.95 | 51.4 | 1.591 | 5.039 | | |
| 19.475 | 27.8 | 1.289 | 4.413 | | |

Example 3: Use of BVP10 Protein in Field Control of Strawberry Red Spider Mites Test agents: 20% avermectin spirodiclofen suspension (Hebei Xingbai Agricultural Technology Co., Ltd., diluted 3000 times during use; and the biological mite pesticide BVP10 with the effective protein concentration of 389.5 µg/mL.

The test included three treatments, each repeated three times; blocks are randomly permuted; and the agents are applied to 3 plants in each block with protective rows provided around the plants. The agents are evenly sprayed to both sides of leaves at dusk (on sunny days) with a 3WBS-16 pressure-controllable manual sprayer, such that the leaves are in full contact with the agents, which does not drip preferably. Ten strawberry plants are taken from each block, with one leaf labeled for each plant. The number of red spider mites on both sides of each of the ten leaves are inspected. The red spider mites are directly observed with a hand-held magnifying lens, and the number of all living mites is taken down. The initial population number of the red spider mites is investigated before the application, and a total of three investigations are conducted on Day 1, Day 4, and Day 7 respectively after the application.

Calculation method of pesticidal effect: the control effect is calculated based on the initial population number of the red spider mites before the application and the number of living red spider mites on each day after the application, and the calculation formula is shown below: The data is analyzed for significance using Duncan's new multiple range method of DPS software.

$$\text{Decline rate of living mites} = \frac{\text{Number of living mites before application} - \text{Number of living mites after application}}{\text{Number of living mites before application}} \times 100\%$$

$$\text{Control effect} = \frac{\text{Decline rate of living mites in treatment blocks} - \text{Decline rate of living mites in control blocks}}{\text{Number of } 100 - \text{Decline rate of living mites in control blockmites before application}} \times 100\%$$

The results of field control effects of several mite pesticides against the strawberry red spider mites are shown in Table 3.

TABLE 3

Pesticidal effects of several mite pesticides against strawberry red spider mites

| Treatment | Initial population number before application | Day 1 after application | | | Day 4 after application | | | Day 7 after application | | |
|---|---|---|---|---|---|---|---|---|---|---|
| | | Residual no of mites | Decline rate (%) of living mites | Control effect (%) | Residual number of mites | Decline rate (%) of living mites | Control effect (%) | Residual number of mites | Decline rate (%) of living mites | Control effect (%) |
| BVP10 protein suspension | 350 | 206 | 41.14 | 79.53 | 234 | 33.14 | 83.71 | 80 | 77.14 | 95.45 |
| 20% Avermectin spirodiclofen diluted by 3000 times | 57 | 33 | 42.11 | 79.86 | 70 | −22.81 | 70.08 | 194 | −240.35 | 32.21 |
| Fresh water as control | 48 | 138 | −187.50 | — | 197 | −310.42 | — | 241 | −402.08 | — |

What is claimed is:

1. A method for controlling tetranychid mites, comprising preparing a pesticide comprising a protein consisting of the amino acid sequence of SEQ ID NO:2, and treating a plant in need of controlling tetranychid mites with the pesticide.

2. The method according to claim 1, where the tetranychid mites are *Tetranychus urticae, Panonychus citri, Tetranychus cinnabarinus*, or strawberry red spider mites.

3. The method according to claim 1, wherein the protein consisting of the amino acid sequence of SEQ ID NO:2 is effective at a median lethal concentration of 19.07 μg/mL against *Tetranychus urticae*.

4. The method according to claim 1, wherein the protein consisting of the amino acid sequence of SEQ ID NO:2 is effective at a median lethal concentration of 58.05 μg/mL against *Panonychus citri*.

5. The method according to claim 1, wherein the protein consisting of the amino acid sequence of SEQ ID NO:2 is effective at a median lethal concentration of 36.08 μg/mL against *Tetranychus cinnabarinus*.

6. The method according to claim 1, wherein the protein consisting of the amino acid sequence of SEQ ID NO:2 is effective at a control effect of 79.53% to 95.45% against strawberry red spider mites.

* * * * *

SEQUENCE LISTING

```
<160> NUMBER OF SEQ ID NOS: 2

<210> SEQ ID NO 1
<211> LENGTH: 270
<212> TYPE: DNA
<213> ORGANISM: Artificial Sequence
<220> FEATURE:
<223> OTHER INFORMATION: DNA sequence for encoding protein

<400> SEQUENCE: 1
atgttaaaaa gtaaaattaa aaaaatagcc ggtgcggctg taattgctgg agcattattg      60
gtttctgtgt cgccagcaaa agcagaaact cttccgggat tgatctgggt catggacaaa     120
tatactgacg cttttaaatt cgacatgttt attaaaaacg gaaatgaaaa atgggtttat     180
gtttacacaa gattatccga tggcaaagtt gatgtggaag aagtaaagtg tgaaacaatt     240
tataaagatc gatgctatgt aaagcagtaa                                       270

<210> SEQ ID NO 2
<211> LENGTH: 89
<212> TYPE: PRT
<213> ORGANISM: Artificial Sequence
<220> FEATURE:
<223> OTHER INFORMATION: Sequence for protein prepared by prokaryotic
      expression, eukaryotic expression, or direct synthesis, based the
      gene sequence of SEQ ID NO 1

<400> SEQUENCE: 2

Met Leu Lys Ser Lys Ile Lys Lys Ile Ala Gly Ala Ala Val Ile Ala
1               5                   10                  15

Gly Ala Leu Leu Val Ser Val Ser Pro Ala Lys Ala Glu Thr Leu Pro
            20                  25                  30

Gly Leu Ile Trp Val Met Asp Lys Tyr Thr Asp Ala Phe Lys Phe Asp
        35                  40                  45

Met Phe Ile Lys Asn Gly Asn Glu Lys Trp Val Tyr Val Tyr Thr Arg
    50                  55                  60

Leu Ser Asp Gly Lys Val Asp Val Glu Glu Val Lys Cys Glu Thr Ile
65                  70                  75                  80

Tyr Lys Asp Arg Cys Tyr Val Lys Gln
                85
```